United States Patent [19]

Zengel et al.

[11] 4,317,947

[45] Mar. 2, 1982

[54] PROCESS FOR THE PREPARATION OF NITROSOBENZENE

[75] Inventors: Hans Zengel, Nordring; Manfred Bergfeld, Erlenbach, both of Fed. Rep. of Germany

[73] Assignee: Akzona Incorporated, Asheville, N.C.

[21] Appl. No.: 190,291

[22] Filed: Sep. 24, 1980

[30] Foreign Application Priority Data

Sep. 29, 1979 [DE] Fed. Rep. of Germany ....... 2939692

[51] Int. Cl.$^3$ ...................... C07C 76/00; C07C 81/02
[52] U.S. Cl. .................................................. 568/949
[58] Field of Search ........................................ 568/949

[56] References Cited

U.S. PATENT DOCUMENTS

| 3,578,720 | 5/1971 | Dodman et al. | 568/949 |
| 3,989,764 | 11/1976 | Woolley | 568/949 |
| 4,178,315 | 12/1979 | Zengel et al. | 568/947 |

FOREIGN PATENT DOCUMENTS 47-31937 11/1972 Japan .................................. 568/949

OTHER PUBLICATIONS

Beilstein, Band V, Sect. I, p. 123, Berlin, (1930).

*Primary Examiner*—Teddy S. Gron
*Attorney, Agent, or Firm*—Francis W. Young; Robert F. Green

[57] ABSTRACT

An improved process for the preparation of nitrosobenzene by catalytically reducing nitrobenzene is disclosed. The improvement comprises performing the reduction in the absence of a reducing agent.

3 Claims, No Drawings

PROCESS FOR THE PREPARATION OF NITROSOBENZENE

BACKGROUND OF THE INVENTION

This invention relates to a process for the preparation of nitrosobenzene by catalytically reducing nitrobenzene.

A brief summary of processes for the production of nitrosobenzene may be found in U.S. Pat. No. 4,178,315 which is incorporated herein by reference and which specifically discloses a process for the preparation of nitrosobenzene by the catalytic reduction of nitrobenzene utilizing as a reducing agent a compound selected from the group consisting of aliphatic compounds containing from about 1 to about 20 carbon atoms, benzene, naphthalene, and ethylenically unsaturated compounds containing from about 2 to about 10 carbon atoms. In the process of said patent the catalyst which is utilized is preferably a mixture of manganese and lead oxides and the reduction is typically carried out at a temperature in the range from about 250° to about 450° C., in the presence of an inert gas such as carbon dioxide, nitrogen, or a noble gas. In the process the activity and selectivity, as well as the life of the catalyst may be increased substantially by subjecting it to a preliminary treatment with a hydrocarbon or hydrogen. Such a process, in which oxygen-free reducing agents instead of the previously customary oxygen-containing reducing agents, are used for the first time, was found to be superior to the known processes with respect to conversion level, selectivity, and catalyst service life. Therefore, a useful industrial process for the preparation of nitrosobenzene by the reduction of nitrobenzene has been provided through the invention in the aforementioned patent.

An improvement on the process of U.S. Pat. No. 4,178,315 is disclosed in German Pat. No. P 2933314 in which it is shown that in the reduction of nitrobenzene, the addition of small quantities of water to the reaction mixture brings about a considerable increase in conversion. According to such a process, the reduction is carried out in the presence of about 0.05 to about 4 mols of water per mol of nitrobenzene, preferably in the presence of about 0.1 to about 2 mols of water per mol of nitrobenzene. It was surprising that, under such conditions, in the absence of a reforming catalyst, the addition of water not only accomplishes the reduction with high selectivity just to the stage of the desired nitrosobenzene, but—compared with the process of U.S. Pat. No. 4,178,315—also brings about an increase in reaction rate.

The object of the present invention is to further improve the process which is disclosed in U.S. Pat. No. 4,178,315, and German Pat. No. P2933314.

SUMMARY OF THE INVENTION

Surprisingly, it has now been found that, under certain conditions, the reduction of nitrobenzene to nitrosobenzene proceeds in the absence of a reducing agent according to an autoredox, or disproportionation mechanism, with high conversion rate and high selectivity. Therefore, the present invention provides a process for the preparation of nitrosobenzene from nitrobenzene in the presence of catalysts known to be used for such a purpose, at temperatures from about 250° to about 450° C., characterized by the fact that the reaction is carried out in the absence of reducing agents known to be used for such a purpose, at pressures in the range from about 0.01 to about 40 bar, if necessary in the presence of nitrogen, carbon dioxide, ammonia, water vapor, an inert gas, or mixtures of these gases.

The catalysts which are useful are all known metal catalysts indicated to be useful in the process of the aforementioned U.S. Pat. No. 4,178,315. In this respect, one may also refer to German Pat. No. 1,810,828, British Pat. Nos. 1,322,531, 1,259,504, 1,251,836, and 1,251,844, Dutch Pat. No. 7,005,588, Japanese Pat. Nos. 47 31 937, 91 26 633, and German Pat. No. 2,346,388.

The catalysts which are utilized are preferably the known manganese oxide/lead oxide catalysts. The catalyst consists of a mixture of manganese and lead oxide applied to a suitable carrier material such as pumice, aluminum oxide, activated carbon, asbestos, brick, or kieselguhr. The atomic ratio of manganese to lead may vary greatly, but in general it is in a range from about 20:1 to about 2:1. Preference is given to catalysts which contain manganese and lead in a ratio of 2 atoms of manganese to one atom of lead. With respect to the preparation of the catalysts to be used in the process of the present invention, one may refer to the detailed statements relating thereto in the aforementioned U.S. patent.

As in the process of the aforementioned U.S. patent, the activity and selectivity, as well as the life of the catalyst may be substantially increased by means of a preliminary treatment of the catalyst by hydrocarbon or with hydrogen. The hydrocarbons which are useful in such a pre-treatment are the compounds already discussed and indicated to be useful as reducing agents. Preferably, the hydrocarbon to be used as the reducing agent is also used for the pre-treatment. The preliminary treatment is performed at a temperature of about 300° to about 400° C. and may last from about 0.5 to about 10 hours.

The process of the present invention may be performed at a temperature from about 250° C. to about 450° C., preferably at a temperature from about 320° to about 410° C. It is therefore not very significant which catalyst and which hydrocarbon are used. In general, the process may be performed at atmospheric pressure, in the gas phase.

It must be considered surprising that, under the mentioned special conditions, reduction of the nitrobenzene is taking place according to an autoredox, or disproportionation mechanism. Of 27 mols nitrobenzene, 2 mols nitrobenzene are split quantitatively into water, nitrogen and carbon dioxide, while 25 mols nitrobenzene are converted to nitrosobenzene. Thus, it is remarkable that no larger quantities of by-products, or cleavage products are formed. The reaction can therefore by represented by the following summation equation:

$$27C_6H_5NO_2 \rightarrow 25C_6H_5NO + 12CO_2 + 5H_2O + N_2$$

The reaction is therefore taking place in the absence of a reducing agent known to be used for the purpose, such as carbon monoxide, aldehydes, ketones, alcohols, or hydrocarbons.

According to one of the two variants of the process pursuant to the invention, the reaction may take place in the presence of nitrogen, carbon dioxide, ammonia, water vapor, or of one of the inert gases, such as helium, neon, or argon. Mixtures of the mentioned gases can also be used, e.g. helium- or neon-containing nitrogen, nitrogen/carbon dioxide, nitrogen/water vapor and carbon dioxide/water vapor mixtures. These gases, or gas mixtures, are inert with respect to the nitro- and nitrosobenzene, as well as the catalyst system. In general, this variant of the process is carried out at atmospheric pressure, i.e. in the gaseous phase. For technical reasons it is often advantageous to operate under a slightly higher pressure, e.g. at pressure up to about 1.5 bar. It is likewise possible to perform the reaction under higher pressures, up to 10 bar, i.e. sometimes in the liquid phase.

According to the other variant of the process pursuant to the present invention, the reaction may take place in the absence of the above-mentioned inert gases. Thus, in this case, only nitrobenzene is supplied to the reaction zone.

The reduction of nitrobenzene pursuant to the invention, according to an autoredox, or disproportionation mechanism, proceeds exothermally. Therefore, in order to maintain the desired reaction temperature, it is necessary to remove the excess heat of reaction as quickly as possible from the reaction mixture. In order to suppress continued reaction of the nitrosobenzene, reaction times are kept as short as possible. Removal of heat and duration of the reaction are regulated by the selection of suitable reaction conditions.

Preferably, the reaction in the absence of the mentioned inert gases is carried out under reduced pressures, in particular about 0.01 to about 0.5 bar. In this case, the reaction mixture is diluted to such an extent so far as the nitrobenzene is concerned, that the accumulating heat of reaction can be removed without any great expenditures for equipment, and reaction times are so short, that the desired high selectivity of the conversion from nitrobenzene to nitrosobenzene is guaranteed.

During the reaction in the presence of one or several of the mentioned inert gases, the conversion is preferably carried out at pressures in the range from about 0.5 to about 5 bar. The quantity of the inert gas to be used in not critical. It is chosen in such a way that, in this variant of the process pursuant to the present invention as well, the partial pressure of the nitrobenzene is not too high, so that the dilution of the reaction mixture required for a rapid removal of heat and for short reaction times is also guaranteed. When such mixtures of nitrobenzene and one or more of the mentioned inert gases are used, the partial pressure of the nitrobenzene preferably is also about 0.01 to about 0.5 bar.

The process pursuant to the present invention can be carried out continuously, as well as discontinuously. For example, in the continuous operation to be considered for an industrial-scale execution of the process, the nitrobenzene is evaporated, preheated if required and, optionally in mixture with the inert gases or vapors, brought into contact with the catalyst under the indicated temperature and pressure conditions. This is advantageously accomplished by conducting the reaction gas over, or through, a catalyst bed in a pipe reactor. Customary packed or fluidized bed technology can thereby be used. The flow velocities of the gases are adapted to the desired contact times. In order to suppress continued reaction of the nitrosobenzene, use is made of reaction times that are as short as possible and thus, in particular when fluidized bed technology is used, of high flow rates. In general, contact times are in a range from about 1 to about 40 seconds, preferably from 1 (1) to 10 seconds.

The process of the present invention may be performed continuously, as well as discontinuously. For example, in the continuous operating method to be considered for an industrial-scale execution of the process, the nitrobenzene is evaporated, and preheated if required, heated to the reaction temperature together with the water vapor and, if required, the inert gas, and then brought into contact with the catalyst. Advantageously the foregoing is performed in such a way that the gas mixture flows over, or through, a catalyst bed in a tube reactor, either in a counter-current or in the same direction. Customary solid, or fluid bed, technology can be employed. The flow velocities of the gases are adapted to the desired contact times. In order to suppress continued reaction of the nitrosobenzene, use is made of contact times that are as short as possible and thus, in particular when fluid bed technology is used, of flow velocities that are high. In general, contact times are in a range from about 0.5 to about 40 seconds, preferably from about 1.0 to about 10 seconds.

The reaction mixture is processed in a simple manner, by quenching it after the catalyst. The nitrosobenzene can be separated from by-products such as aniline, azo- and azoxybenzene, as well as from unreacted nitrobenzene, by fractional distillation. When water vapor is used, the water is eliminated as separate, liquid phase. It can be removed in a simple manner and immediately returned again to the reactor. Unreacted nitrobenzene and inert gas, as the case may be, can be circulated.

In the execution of the version according to which the catalyst, before it comes into contact with the nitrobenzene, is subjected to a preliminary treatment, it is expedient to proceed in such a way that the catalyst, after it has been dried, is transferred to the reactor were it is treated with a hydrocarbon or with hydrogen at about 400° C. for about 2 hours with exclusion of air, whereupon the nitrobenzene, if required in mixture with an inert gas, is gradually supplied. A gradual decline in catalyst activity occurring after continuous operation for many weeks can easily be reversed in such a way that, during operation of the reactor, while maintaining the reaction temperature, the supply of nitrobenzene is temporarily interrupted and the catalyst is instead flushed for several hours with a hydrocarbon, or hydrogen.

Compared with the known processes for the preparation of nitrosobenzene, the process pursuant to the invention possesses considerable advantages.

No reducing agents and auxiliary materials are required in the execution of the process pursuant to the invention. This makes the process economical, as well as simple, so far as operation and processing of the reaction mixture are concerned. The variant of the process pursuant to the invention according to which reduction is carried out in the presence of an inert gas is likewise advantageous compared with the known processes, because no reducing agent is required, so that no products of a reaction with the latter will accumulate and have to be separated.

The present invention will be further described in the following and non-limiting examples.

CATALYST PREPARATION 1

The carrier used was pumice, comminuted to an average diameter of about 1 mm, which has been impregnated with an aqueous solution of a mixture of lead and manganese nitrate (Pb/Mn = 1/2 mol/mol) and dried at 50° C. under a vacuum in a rotary evaporator. The catalyst was then treated for about 2 hours at 400° C. with access of air, whereupon it was used in the reaction.

CATALYST PREPARATION 2

First, the procedure as in Catalyst Preparation 1 was followed. After that, however, the catalyst, once it had been dried in the rotary evaporator, was immediately placed in the reactor and there treated for 2 hours at about 400° C. with methane. Great care was taken, that all air was excluded. Then, the methane was replaced by nitrobenzene and the reactor started.

CATALYST PREPARATION 3

α-Aluminum oxide spherules with a diameter of 0.8 to 1.2 mm were used as carriers for the catalyst. They were impregnated with an aqueous solution of a mixture of lead and manganese nitrate (molar ratio Pb/Mn=1:2) and dried at 120° C. under a vacuum. Subsequently, the catalyst was placed in the reactor and there treated for 2 hours at 400° C. with methane.

CATALYST PREPARATION 4

Silicon dioxide spherules with a diameter of 0.8 to 1.2 mm were impregnated with an aqueous solution of a mixture of lead and manganese nitrate with a molar ratio of lead/manganese of 1:2 and dried in a vacuum at 100° C. Subsequently, the catalyst was introduced into the reactor, where it was treated with nitrogen for 2 hours at 380° C.

EXAMPLES 1–6

A mixture of nitrobenzene and nitrogen, preheated to 396° C., was continuously conducted through a glass pipe with an inside diameter of 1 cm and a length of about 50 cm, which contained 16 cc of a freshly prepared Pb/Mn catalyst (catalyst preparation 1) in the form of 1 mm spherules. The throughput was 27 g/hour (0.22 mol) of nitrobenzene and 45 Nlit/hour of nitrogen. After leaving the reaction pipe, which, by means of electrical heating, was kept practically isothermally at 396° C., the reaction mixture was indirectly cooled with water to 25° C. and the constituents of low volatility were separated. The small quantities of compounds with low volatility still present in the exhaust gas were subsequently absorbed by a washer filled with dioxane. A nitrobenzene conversion of 17% was obtained under these conditions, whereby nitrosobenzene had been formed with a selectivity of 89%. The remainder of the solution was composed of azobenzene, azoxybenzene and aniline. The reactor was operated continuously for a total of 10 hours, during which it was not possible to determine any decline in the activity of the catalyst. A gas-chromatographic investigation of the exhaust gas showed only carbon dioxide and water in addition to nitrogen, as well as traces of nitrosobenzene and nitrobenzene. The following Table I shows the yields and selectivities in dependence upon the duration of operation.

TABLE I

| EXAMPLE NO. | DURATION OF OPERATION HRS. | TEMPERATURE °C. | CONVERSION MOL % | $C_6H_5NO$ MOL % | SELECT MOL % $C_6H_5NO$ | ANILINE MOL % | AZO-BENZ. MOL % | AZOXY-BENZ. MOL % |
|---|---|---|---|---|---|---|---|---|
| 1 | 1 | 395 | 17.4 | 15.49 | 89.0 | 0.32 | 0.28 | 0.51 |
| 2 | 2 | 395 | 17.22 | 15.39 | 89.4 | 0.22 | 0.15 | 0.36 |
| 3 | 3 | 395 | 17.7 | 15.7 | 88.7 | 0.28 | 0.18 | 0.41 |
| 4 | 5 | 395 | 17.95 | 15.8 | 88.0 | 0.33 | 0.17 | 0.46 |
| 5 | 7.5 | 390 | 17.05 | 15.24 | 89.4 | 0.18 | 0.12 | 0.34 |
| 6 | 10 | 398 | 18.0 | 15.93 | 88.8 | 0.26 | 0.20 | 0.41 |

EXAMPLES 7–13

15 g. of a freshly prepared lead/manganese catalyst (catalyst preparation 2), in the form of 1 mm granules were placed in the same experimental set-up as in Examples 1 to 6, and a mixture of nitrobenzene and carbon dioxide, heated to 325° C., was continuously conducted through the reactor. The throughput was 27 g/hr. (0.22 mol) of nitrobenzene and 40 Nlit/hr. of carbon dioxide. Processing was performed analogous to Examples 1 to 6. Yields and selectivities, in dependence upon the duration of operation, are compiled in the following Table II.

TABLE II

| EXAMPLE NO. | DURATION OF OPERATION HRS. | TEMPERATURE °C. | CONVERSION MOL % | $C_6H_5NO$ MOL % | SELECT MOL % $C_6H_5NO$ | ANILINE MOL % | AZO-BENZ. MOL % | AZOXY-BENZ. MOL % |
|---|---|---|---|---|---|---|---|---|
| 7 | 1 | 325 | 12.58 | 11.01 | 87.5 | 0.37 | 0.27 | <0.1 |
| 8 | 2 | 325 | 11.78 | 10.27 | 87.18 | 0.40 | 0.24 | <0.1 |
| 9 | 3 | 325 | 12.62 | 11.18 | 88.59 | 0.27 | 0.25 | <0.1 |
| 10 | 4 | 328 | 14.72 | 12.99 | 88.25 | 0.41 | 0.24 | <0.1 |
| 11 | 5 | 325 | 13.88 | 12.23 | 88.11 | 0.32 | 0.23 | <0.1 |
| 12 | 6 | 325 | 13.76 | 12.15 | 88.30 | 0.18 | 0.23 | <0.1 |
| 13 | 7 | 328 | 14.35 | 12.56 | 87.53 | 0.33 | 0.23 | 0.16 |

EXAMPLES 14–18

In the same experimental set-up as in Examples 7–13 and under otherwise identical reaction conditions, 27 g/hr. (0.22 mol) of nitrobenzene and a mixture of 13.33 Nlit/hr. of nitrogen and 26.66 Nlit/hr. of carbon dioxide were reacted continuously at 325° C. Yields and selectivities, in dependence upon the duration of operation, are compiled in the following Table III. One can see therefrom, that yields and selectivities depend only upon the quantity of the inert gas, and not upon the kind of the inert gas pursuant to the invention (the total quantity of the two inert gases corresponds to that Examples 7–13).

TABLE III

| EXAMPLE NO. | DURATION OF OPERATION HRS. | TEMPERATURE °C. | CONVERSION MOL % | $C_6H_5NO$ MOL % | SELECT MOL % $C_6H_5NO$ | ANILINE MOL % | AZO-BENZ. MOL % | AZOXY-BENZ. MOL % |
|---|---|---|---|---|---|---|---|---|
| 14 | 1 | 325 | 11.74 | 10.32 | 87.90 | 0.34 | 0.29 | <0.1 |
| 15 | 2 | 335 | 13.07 | 11.49 | 87.91 | 0.36 | 0.25 | <0.1 |
| 16 | 3 | 335 | 13.83 | 11.93 | 86.26 | 0.41 | 0.29 | 0.19 |
| 17 | 4 | 325 | 12.74 | 10.99 | 86.26 | 0.35 | 0.28 | 0.18 |
| 18 | 5 | 330 | 13.06 | 11.19 | 85.68 | 0.37 | 0.32 | 0.21 |

EXAMPLES 19-24

Analogous to Examples 1 to 6, a metal pipe of 50 cm length and an inside diameter of 30 mm was filed with 45 g. of a freshly prepared Pb/Mn catalyst (catalyst preparation 3) in the form of 0.8 mm spherules and heated to 335° C., whereupon a gas mixture consisting of nitrobenzene and helium, preheated to the same temperature, was continuously passed through. The throughput amounted to 27 g/hr. (0.22 mol) of nitrobenzene and 40 Nlit/hr. of helium. Yields and selectivities, in dependence upon the duration of operation, are again compiled in the following Table IV.

TABLE IV

| EXAMPLE NO. | DURATION OF OPERATION HRS. | TEMPERATURE °C. | CONVERSION MOL % | $C_6H_5NO$ MOL % | SELECT MOL % $C_6H_5NO$ | ANILINE MOL % | AZO-BENZ. MOL % | AZOXY-BENZ. MOL % |
|---|---|---|---|---|---|---|---|---|
| 19 | 1 | 335 | 13.28 | 11.55 | 86.97 | 0.28 | 0.28 | 0.22 |
| 20 | 2 | 335 | 12.57 | 10.85 | 86.32 | 0.29 | 0.27 | 0.22 |
| 21 | 3 | 335 | 12.40 | 10.71 | 86.37 | 0.34 | 0.26 | 0.17 |
| 22 | 4 | 335 | 13.05 | 11.32 | 86.74 | 0.32 | 0.25 | 0.20 |
| 23 | 5 | 335 | 12.66 | 10.81 | 85.39 | 0.46 | 0.27 | 0.18 |
| 24 | 6 | 335 | 12.11 | 10.67 | 88.11 | 0.32 | 0.22 | <0.1 |

EXAMPLES 25-29

Analogous to Examples 19-24, 45 g. of a freshly prepared Pb/Mn catalyst (catalyst preparation 4) in the form of 0.8 to 1 mm spherules were heated to 335° C., and a gas mixture of nitrobenzene and ammonia, preheated to the same temperature, was continuously conducted through the reactor. The throughput amounted to 27 g/hr. (0.22 mol) of nitrobenzene and 40 Nlit/hr. (1.79 mol/hr.) of ammonia. Processing was carried out analogous to Examples 1 to 6. Yields and selectivities, in dependence upon the duration of operation, are compiled in the following Table V.

EXAMPLES 30-34

Analogous to Examples 1 to 6, 13.6 g. of a freshly prepared Pb/Mn catalyst (catalyst preparation 1) in the form of 1 mm spherules were heated to 337° C., and gas mixture of nitrobenzene and water vapor, preheated to the same temperature, was, via an evaporator, conducted through the reactor. The throughput amounted to 27 g/hr. (0.22 mol) of nitrobenzene and 2.2 mol/hr. of water vapor. After leaving the reaction zone, the gaseous reaction mixture was condensed in a cooler and checked for its composition by means of gas chromatography. Yields and selectivities, in dependence upon the duration of operation, are compiled in the following Table VI.

TABLE VI

| EXAMPLE NO. | DURATION OF OPERATION HRS. | TEMPERATURE °C. | CONVERSION MOL % | $C_6H_5NO$ MOL % | SELECT MOL % $C_6H_5NO$ | ANILINE MOL % | AZO-BENZ. MOL % | AZOXY-BENZ. MOL % |
|---|---|---|---|---|---|---|---|---|
| 30 | 1 | 337 | 18.14 | 15.8 | 87.10 | 0.8 | <0.1 | <0.1 |
| 31 | 2 | 337 | 20.52 | 17.1 | 83.33 | 1.0 | 0.2 | 0.6 |
| 32 | 3 | 339 | 20.95 | 17.9 | 85.44 | 1.1 | 0.3 | <0.1 |
| 33 | 4 | 332 | 23.76 | 19.7 | 82.91 | 1.4 | 0.3 | 0.5 |
| 34 | 5 | 340 | 24.84 | 21.1 | 84.94 | 1.3 | 0.3 | 0.3 |

EXAMPLES 35-38

350 cc of a freshly prepared Pb/Mn catalyst (catalyst preparation 2) were filled into a stainless steel reactor of 465 cm length and an inside diameter of 33.5 mm, and heated to 340° C. Then, 136 g/hr. (1.1 mol) of nitrobenzene and 80 g/hr. (4.4 mol) of water were metered in at the same temperature via an evaporator. Simultaneously, 500 lit/hr. of gas were returned to the reactor with a circulating pump. 40 Nlit/hr. of carbon dioxide were continuously metered in via a mixing valve, whereby the circulating quantity was kept constant by

TABLE V

| EXAMPLE NO. | DURATION OF OPERATION HRS. | TEMPERATURE °C. | CONVERSION MOL % | $C_6H_5NO$ MOL % | SELECT MOL % $C_6H_5NO$ | ANILINE MOL % | AZO-BENZ. MOL % | AZOXY-BENZ. MOL % |
|---|---|---|---|---|---|---|---|---|
| 25 | 1 | 335 | 11.99 | 10.7 | 89.24 | 0.4 | <0.1 | <0.1 |
| 26 | 2 | 335 | 11.45 | 10.3 | 89.96 | 0.3 | <0.1 | <0.1 |
| 27 | 3 | 335 | 10.80 | 9.7 | 89.81 | 0.3 | <0.1 | <0.1 |
| 28 | 4 | 335 | 8.96 | 8.1 | 90.40 | 0.2 | <0.1 | <0.1 |
| 29 | 5 | 335 | 8.75 | 7.9 | 90.28 | 0.2 | <0.1 | <0.1 | also withdrawing about 40 Nlit/hr. The gaseous reaction mixture was condensed in a cooler and withdrawn continuously. An aqueous and an organic phase were formed thereby, which were investigated for their content of nitro/nitrosobenzene, anilene, azo- and azoxybenzene by means of gas chromatography. Yields and selectivities, again in dependence upon the duration of operation, are compiled in the following Table VII.

TABLE VII

| EXAMPLE NO. | DURATION OF OPERATION HRS. | TEMPERATURE °C. | CONVERSION MOL % | $C_6H_5NO$ MOL % | SELECT MOL % $C_6H_5NO$ | ANILINE MOL % | AZO-BENZ. MOL % | AZOXY-BENZ. MOL % |
|---|---|---|---|---|---|---|---|---|
| 35 | 1 | 340 | 29.48 | 23.4 | 79.37 | 2.2 | 0.6 | 1.1 |
| 36 | 2 | 338 | 20.78 | 23.8 | 77.32 | 2.4 | 0.7 | 1.6 |
| 37 | 3 | 341 | 32.40 | 25.6 | 79.01 | 2.3 | 0.7 | 1.4 |
| 38 | 4 | 342 | 33.26 | 26.1 | 78.47 | 2.6 | 0.7 | 1.4 |

EXAMPLE 39

The experimental apparatus described for Examples 19 to 24 was filled with 45 g. of a freshly prepared Pb/Mn catalyst in the form of 1.2 mm spherules (catalyst preparation 4), heated to 366° C., and a nitrobenzene vapor preheated to reaction temperature (330° C.) was conducted through the reactor under a pressure of 0.1 bar. After leaving the reactor, the reaction mixture was first quenched by means of a water cooler and the still volatile constituents then frozen out by means of several succeeding cold traps filled with dry ice. After that, the contents were again determined by means of gas chromatography. At a throughput of 13.5 g/hr. (0.11 mol) of nitrobenzene, 59% of the charged nitrobenzene were thereby converted, the yield amounting to 44.8% of nitrosobenzene, 1.57% of aniline, 2.93% of azobenzene and 0.5% of azoxybenzene.

EXAMPLE 40

Using the same experimental arrangement as in Example 39, as well as the same catalyst filling, a mixture of nitrobenzene and helium, heated to 335° C., was, under otherwise identical conditions, continuously converted at a pressure of 3 bar. Throughput amounted to 54 g/hr. (0.44 mol) of nitrobenzene and 120 Nlit/hr. of helium. Processing was performed as already described in previous experiments. After 1 hour of operation, a gas-chromatographic investigation of the product mixture produced the following composition of the reaction mixture:

| | |
|---|---|
| nitrosobenzene | 15.1 mol % |
| aniline | 0.3 mol % |
| azobenzene | <0.1 mol % |
| azoxybenzene | <0.1 mol % |

The conversion rate was 16.2%.

EXAMPLE 41

The experimental apparatus described for Examples 19 to 24 was filled with 45 g. of a freshly prepared Pb/Mn catalyst in the form of 1.2 mm spherules (catalyst preparation 4), heated to 345° C. and, under a pressure of 0.5 bar, a nitrobenzene vapor heated to the reaction temperature (330° C.) conducted through the reactor. After emergence from the reactor, the reaction mixture was first quenched by means of a water cooler and the still volatile constituents frozen out by means of several succeeding cold traps filled with dry ice. The following content determination was again performed by means of gas-chromatography. Thereby, at a throughput of 13.5 g/hr. (0.11 mol) of nitrobenzene, 52% of the charged nitrobenzene were converted. The yield data were 36.4% nitrosobenzene, 1.5% aniline, 2.75% azobenzene, and 0.6% azoxybenzene.

What is claimed is:

1. A process for the preparation of nitrosobenzene from nitrobenzene in the presence of catalysts at temperatures from about 250° to about 450° C., characterized by the fact that the reaction time is from about 0.5 to about 40 seconds, excess heat of reaction is removed and the reaction is carried out in the absence of reducing agents and at pressures in the range from about 0.01 to about 40 bar.

2. The process of claim 1 wherein the reaction is performed in the presence of a gas or a mixture of gases selected from the group consisting of gases which are inert with respect to the nitrosobenzene, nitrobenzene, and catalysts, at a partial pressure of the nitrobenzene in the range from about 0.01 to about 0.5 bar.

3. The process of claim 2 wherein the reaction is performed in the presence of one or more of the gases at a total pressure in the range from about 0.5 to about 5 bar and at a partial pressure of the nitrobenzene from about 0.01 to about 0.5 bar.

* * * * *